(12) United States Patent
Willbold et al.

(10) Patent No.: US 10,889,618 B2
(45) Date of Patent: *Jan. 12, 2021

(54) D-ENANTIOMERIC PEPTIDES DERIVED FROM D3 AND USE THEREOF

(71) Applicant: FORSCHUNGSZENTRUM JUELICH GMBH, Juelich (DE)

(72) Inventors: Dieter Willbold, Juelich (DE); Susanne Aileen Funke, Sonnefeld (DE); Oleksander Brener, Duesseldorf (DE); Luitgard Nagel-Steger, Langenfeld (DE); Dirk Bartnik, Cologne (DE); Antonia Nicole Klein, Dueren (DE)

(73) Assignee: FORSCHUNGSZENTRUM JUELICH GMBH, Juelich (DE)

( * ) Notice: Subject to any disclaimer, the term of this patent is extended or adjusted under 35 U.S.C. 154(b) by 0 days.

This patent is subject to a terminal disclaimer.

(21) Appl. No.: 16/200,820

(22) Filed: Nov. 27, 2018

(65) Prior Publication Data

US 2019/0085030 A1    Mar. 21, 2019

Related U.S. Application Data

(63) Continuation of application No. 15/482,968, filed on Apr. 10, 2017, now Pat. No. 10,167,318, which is a continuation of application No. 14/426,797, filed as application No. PCT/EP2013/068992 on Sep. 13, 2013, now abandoned.

(30) Foreign Application Priority Data

Sep. 14, 2012 (DE) .......................... 10 2012 108 598

(51) Int. Cl.
| | |
|---|---|
| *C07K 7/08* | (2006.01) |
| *C07K 14/47* | (2006.01) |
| *A61K 38/08* | (2019.01) |
| *A61K 38/10* | (2006.01) |
| *C07K 7/06* | (2006.01) |
| *A61K 38/00* | (2006.01) |
| *G01N 33/68* | (2006.01) |

(52) U.S. Cl.
CPC ................ *C07K 7/08* (2013.01); *A61K 38/08* (2013.01); *A61K 38/10* (2013.01); *C07K 7/06* (2013.01); *C07K 14/4711* (2013.01); *G01N 33/6896* (2013.01); *A61K 38/00* (2013.01); *G01N 2333/4709* (2013.01); *G01N 2410/00* (2013.01)

(58) Field of Classification Search
CPC ........ A61K 38/00; A61K 38/08; A61K 38/10; C07K 7/06; C07K 7/08; C07K 14/4711; G01N 2333/4709; G01N 33/6896; G01N 2410/00

See application file for complete search history.

(56) References Cited

FOREIGN PATENT DOCUMENTS

WO    WO-02081515 A2 * 10/2002 ............... C07K 7/08

* cited by examiner

*Primary Examiner* — Gregory S Emch
(74) *Attorney, Agent, or Firm* — Abel Schillinger, LLP

(57) ABSTRACT

The present invention relates to novel D-enantiomeric A-beta-oligomer-binding peptides, homologs, fragments, parts and polymers thereof and use thereof.

18 Claims, 2 Drawing Sheets

Specification includes a Sequence Listing.

D-ENANTIOMERIC PEPTIDES DERIVED FROM D3 AND USE THEREOF

CROSS-REFERENCE TO RELATED APPLICATIONS

The present application is a continuation of U.S. application Ser. No. 15/482,968, filed Apr. 10, 2017, which is a continuation of U.S. application Ser. No. 14/426,797, filed Mar. 9, 2015, which is a National Stage of PCT/2013/068992 filed Sep. 13, 2013. The entire disclosures of these applications are expressly incorporated by reference herein.

SEQUENCE LISTING

The instant application contains a Sequence Listing which has been submitted electronically in ASCII format and is hereby incorporated by reference in its entirety. Said ASCII copy, created on Jul. 6, 2017, is named 6509-P50376_SL.txt and is 3,756 bytes in size.

BACKGROUND OF THE INVENTION

1. Field of the Invention

The present invention relates to novel D-enantiomeric A-beta-oligomer-binding peptides derived from D3 and use thereof, particularly in medicine.

2. Discussion of Background Information

Due to the demographic development in the coming decades, the number of people suffering from age-related diseases will increase. Particularly noteworthy here is so-called Alzheimer's disease (AD, Alzheimer's dementia, latin=Morbus Alzheimer).

A feature of Alzheimer's disease are extracellular deposits of amyloid beta peptide (A-beta peptide). This deposition of A-beta peptide in plaques is typically determined post mortem in the brains of AD patients. Therefore, various forms of A-beta peptide—such as fibrils—are blamed for the emergence and progression of the disease. In addition, for some years the small, freely diffusible A-beta oligomers have been recognized as the major cause of the emergence and progress of AD.

A-beta monomers, as building blocks of A-beta oligomers, form continuously in the human body and are probably not toxic per se. They may even have a neuroprotective function. A-beta monomers can be randomly stored together depending on their concentration. The concentration is dependent on their rate of formation and rate of degradation in the body. An increase in the concentration of A-beta monomers occurs in the body with increasing age, such that spontaneous aggregation of the monomers to form A-beta oligomers is more likely. The A-beta oligomers thus formed could proliferate in analogy to prions and eventually lead to Alzheimer's disease.

No active ingredient or medicament currently exists that has an effect on the causes of AD. The medicaments currently used and approved alleviate some of the symptoms that occur in AD. However, they are not capable of slowing the disease progression or of bringing about a cure. Some substances exist which have shown success in animal experiments in the prevention, but not (necessarily) in the treatment, of AD.

An important difference between prevention and treatment or even cure of AD lies in the fact that prevention can potentially be achieved by preventing the formation of the first A-beta oligomers. A few A-beta ligands are adequate for prevention which do not necessarily have high affinity or selectivity with regard to A-beta oligomers.

The formation of A-beta oligomers from numerous monomers is a higher order reaction and is therefore dependent to a high degree on the A-beta monomer concentration. Therefore, a small reduction in the active A-beta monomer concentration already leads to prevention of the formation of the first A-beta oligomers. The preventive therapeutic concepts and substances currently in development are based on this mechanism.

In the treatment of AD, however, a completely new situation could be initiated. Here, A-beta oligomers or possibly also even larger polymers or fibrils are present which proliferate by prion-like mechanisms. However, this proliferation is a lower order reaction and is therefore scarcely dependent on the A-beta monomer concentration.

The substances known from the prior art reduce the concentration of A-beta monomers and/or oligomers in a variety of ways. For instance, gamma secretase modulators are known, which have been used for prevention in animal experiments.

Various sequences of D-amino acids which bind to A-beta peptides are known from WO 02/081505. These sequences of D-amino acids bind to amyloid beta peptides with a dissociation constant ($K_D$) of 4 μmol.

Hybrid compounds, consisting of aminopyrazoles and peptides which prevent A-beta oligomerization, are known from WO 2011/147797.

For many substances which have shown positive results in animal experiments, this effect could not be confirmed in human clinical trials. In phase II and III clinical trials, only people who have been clearly diagnosed with AD are allowed to be treated. In this case, a small reduction in the A-beta monomer concentration is no longer adequate to prevent the formation of even more A-beta oligomers from those already present, e.g. by a prion-like mechanism. However, the proliferation of A-beta oligomers or even better their destruction or neutralization is absolutely necessary in order to influence the course of the disease.

Currently, AD is mainly diagnosed by neuropsychological tests by examining people in whom symptoms of dementia have already occurred. It is known, however, that A-beta oligomers and the fibrils and plaques formed therefrom over time in the course of the disease occur up to 20 years before the onset of symptoms in the brain of patients, and may have already caused irreversible damage. However, in practice there is currently no possibility of diagnosing AD before the outbreak of symptoms.

Thus, there still exists a requirement for novel compounds (active ingredients) which bind very specifically and with high affinity to A-beta oligomers, and thus prevent their proliferation. Said compounds should have no undesirable side effects and in particular not provoke any immune response. The compounds should also recognize toxic A-beta oligomers and therefore also the small, freely diffusible oligomers at low concentrations, and completely destroy and/or prevent the (prion-like) proliferation thereof.

Furthermore, there exists a need for novel compounds which can be used as probes for the detection and labelling of A-beta oligomers, in particular if the disease is not well advanced and the oligomers only occur at low concentrations.

A further object of the present invention was to provide substances which not only focus on extracellular A-beta peptides, like most compounds known from the prior art, but specifically bind soluble A-beta oligomers. Furthermore, the novel compounds should inhibit or prevent formation of fibrils of A-beta peptides.

It was also an object to provide novel peptides, preferably derivatives of the D-enantiomeric D-peptide D3 (SEQ ID NO: 11), which have efficient properties compared to D3. The properties include, inter alia, binding affinity and specificity for A-beta species, inhibition of A-beta fibril formation, inhibition of A-beta cytotoxicity, precipitation of A-beta oligomers and conversion of A-beta fibrils to non-toxic, non-amyloidogenic species.

SUMMARY OF THE INVENTION

This object is achieved by a peptide comprising an amino acid sequence according to SEQ ID NO: 1 (D3-Delta-HTH), SEQ ID NO: 2 (RD2), SEQ ID NO: 3 (RD1), SEQ ID NO: 4 (RD3), SEQ ID NO: 5 (DB3), SEQ ID NO: 6 (NT-D3), SEQ ID NO: 7 (DB1), SEQ ID NO: 8 (DB2), SEQ ID NO: 9 (DB4) and/or SEQ ID NO. 10 (DB5) and/or homologs, fragments and parts thereof. This object is also achieved by polymers of the SEQ ID NO: 1 (D3-Delta-HTH), SEQ ID NO: 2 (RD2), SEQ ID NO: 3 (RD 1), SEQ ID NO: 4 (RD3), SEQ ID NO: 5 (DB3), SEQ ID NO: 6 (NT-D3), SEQ ID NO: 7 (DB1), SEQ ID NO: 8 (DB2), SEQ ID NO: 9 (DB4) and/or SEQ ID NO. 10 (DB5) and/or homologs thereof.

Fragments and parts show a similar or identical effect to the peptides according to the invention.

In one variant, the peptides according to SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9 and/or SEQ ID NO. 10 and homologs thereof consist substantially and preferably of at least 60%, 75%, 80%, particularly preferably 85%, 90%, 95%, in particular 96%, 97%, 98%, 99%, 100% of D-amino acids.

A polymer in the context of the invention is formed from 2, 3, 4, 5, 6, 7, 8, 9, 10, 11, 12, 13, 14, 15, 16, 17, 18, 19, 20 or more monomers selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9 and/or SEQ ID NO. 10 and homologs thereof, which for already A-beta oligomer. The polymers according to the invention are composed of identical monomers or a combination of 2, 3, 4, 5, 6, 7, 8, 9 or 10 different monomers, different to the abovementioned monomers, as so-called combination polymers. The monomers may also be, in part, identical. The number of identical monomers in the combination polymers is arbitrary.

In one alternative, the combination polymers comprise at least one monomer selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO. 10 and/or SEQ ID NO: 11 and homologs thereof and also parts or fragments thereof and at least one A-beta-oligomer-binding peptide which differs from the monomers selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO. 10 and/or SEQ ID NO: 11 and homologs thereof and also parts or fragments thereof, preferably of substantially D-enantiomers, as a further monomer.

Polymers may be prepared, for example, via chemical synthesis or peptide synthesis.

In one embodiment of the invention, the monomers are covalently linked to one another. In a further embodiment, the monomers are non-covalently bound to one another.

A covalent binding or linking of the monomer units is present in the context of the invention if the peptides are linearly linked head-to-head, tail-to-tail or head-to-head with one another without intervening linker or linker groups being used.

A non-covalent linking is present in the context of the invention if the monomers are linked to one another via biotin and streptavidin, particularly streptavidin tetramer.

In one variant of the present invention, the monomers may be linked together linearly, in particular as described above. In another variation, the monomers are linked together branched to give the polymer according to the invention.

A branched polymer according to the invention can be a dendrimer, in which the monomers are linked together covalently or non-covalently.

Alternatively, the monomers may also be linked to a platform molecule (such as PEG or sugar) and thus form a branched polymer.

Alternatively, combinations of these options are also possible.

Monomers and polymers are hereinafter referred to as peptides according to the invention.

One variant of the invention is a peptide having the amino acid sequence according to SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9 and/or SEQ ID NO. 10 and/or homologs thereof with an identity of 50%.

In the context of the invention, "homologous sequences" or "homologs" signifies that an amino acid sequence has an identity with any of the abovementioned amino acid sequences of the monomers of at least 50, 55, 60, 65, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100%. In place of the word "identity", the terms "homologous" or "homology" are used synonymously in the present description. The identity between two nucleic acid sequences or polypeptide sequences is calculated by comparison with the BESTFIT program based on the algorithm of Smith, T. F. and Waterman, M. S (Adv. Appl. Math. 2: 482-489 (1981)) setting the following parameters for amino acids: Gap creation penalty: 8 and Gap extension penalty: 2; and the following parameters for nucleic acids: Gap creation penalty: 50 and Gap extension penalty: 3. Preferably, the identity between two nucleic acid sequences or polypeptide sequences is defined by the identity of the nucleic acid sequence/polypeptide sequence respectively over the entire sequence length, which is calculated by comparison using the GAP program based on the algorithm of Needleman, S. B. and Wunsch, C.D. (J. Mol. Biol. 48: 443-453) setting the following parameters for amino acids: Gap creation penalty: 8 and Gap extension penalty: 2; and the following parameters for nucleic acids: Gap creation penalty: 50 and Gap extension penalty: 3.

In the context of the present invention, two amino acid sequences are identical if they have the same amino acid sequence.

In one variant, homologs are understood to mean the corresponding retro-inverso sequences of the monomers mentioned above. The term "retro-inverso sequence", in accordance with the invention, refers to an amino acid sequence which is composed of amino acids in the enantiomeric form (inverso: chirality of the alpha-carbon atom inverted) and in which the sequence order has also been reversed compared to the original amino acid sequence (retro=backwards).

In a further variant, the peptides according to the invention bind to parts of the amyloid beta peptide.

In a further variant, the peptides according to the invention have sequences which differ from the specified sequences by up to three amino acids.

Furthermore, sequences are also used as peptides which comprise the sequences mentioned above.

In a further variant, the peptides have fragments of the abovementioned sequences or have sequences homologous to the abovementioned sequences.

The invention relates to a peptide for use in medicine, preferably for the treatment of Alzheimer's disease.

In one embodiment of the present invention, the peptide is largely composed of D-amino acids.

In the context of the present invention, the term "largely composed of D-amino acids" signifies that the monomers to be used according to the invention are made up of at least 50%, 60%, preferably 75%, 80%, particularly preferably 85%, 90%, 95%, in particular 96%, 97%, 98%, 99% or 100% of D-amino acids.

In one embodiment of the present invention, the peptides according to the invention are derivatives of the D-enantiomeric D-peptide D3. Derivatives in the context of the invention are peptide sequences derived from D3 which are achieved by one of the following three methods:

a) changing the order and/or number of amino acid residues in D3. In this case, amino acids are only used which are present in the D3 sequence.
 b) deleting 1, 2, 3, 4, 5, 6, 7, 8, 9, 10 or 11 amino acids of the D3 sequence.
 c) exchanging 1, 2, 3, 4, 5 or 6 amino acids with other amino acids, preferably D-enantiomers.

In a further variant, the invention relates to a peptide for the inhibition of formation of fibrils of amyloid beta peptides. The polymers according to the invention detoxify the A-beta oligomers or polymers formed therefrom, and also fibrils, by binding thereto and thus converting them into non-toxic compounds. Accordingly, the present invention also provides a method for detoxifying A-beta oligomers, polymers formed therefrom or fibrils.

The invention also relates in one embodiment to peptides in accordance with the invention which are linked to a further substance.

In the context of the invention, the linking takes the form of a chemical bond as defined in Römpp Chemie Lexikon, 9th Edition, Volume 1, page 650 ff, Georg Thieme Verlag Stuttgart, preferably a main valency bond, particularly a covalent bond.

In one variant, the substances are medicaments or active ingredients, defined according to the Medicines Act § 2 or § 4 (19), as of September 2012. In one alternative, active ingredients are therapeutically active substances which are used as medicinally active substances. Anti-inflammatories are preferably used.

In a further variant, the substances are compounds which enhance the effect of the peptides.

In one alternative, such compounds are aminopyrazole and/or aminopyrazole derivatives. Aminopyrazole derivatives in the context of the invention are 3-aminopyrazole-5-carboxylic acid or 3-nitropyrazole-5-carboxylic acid and also all derivatives thereof in which the heterocyclic CH group has been replaced by —CR— or —N— or —O— or —S—, and also all peptidic dimers, trimers or tetramers, preferably aminopyrazole trimer, derived therefrom.

In a further alternative, said compounds are compounds which improve the solubility of the peptides and/or passage of the blood-brain barrier.

In one alternative, the peptides according to the invention have any desired combination of at least two or more features of the variants, embodiments and/or alternatives described above.

The invention also relates to a peptide in accordance with the invention for binding to aggregated A-beta peptides.

The invention further relates to a method for preparing the peptide according to the invention by peptide synthesis, as is known to those skilled in the art, for example, organic synthetic methods for any compounds with low molecular weights (low-molecular weight compounds) and/or mutagenesis and recombinant preparation.

The invention also relates to a composition comprising the peptide according to the invention, particularly for the treatment of Alzheimer's disease.

The present invention also relates to a composition comprising the peptide according to the invention, particularly for preventing toxic A-beta oligomers, or for destroying polymers or fibrils formed therefrom.

The "composition" according to the invention may be, for example, a vaccine, a medicament (e.g. in tablet form), an injectable solution, a food or food supplement, comprising the peptide according to the invention in a formulation being prepared due to technical expertise.

The invention also relates to a kit comprising the peptide according to the invention.

In such a kit, the peptides according to the invention may be packaged in containers, optionally with/in buffers or solutions. All components of the kit can be packaged in the same container or separately. Furthermore, the kit may include instructions for use. Such a kit may comprise, for example, in accordance with the invention, in an injection vial with a stopper and/or septum. Furthermore, a disposable syringe can also be contained therein.

The present invention further relates to the use of the peptide according to the invention as a probe for the identification and qualitative and/or quantitative determination of amyloid beta oligomers or fibrils.

The present invention also relates to a probe comprising the peptide according to the invention for the identification and qualitative and/or quantitative determination of amyloid beta oligomers.

Such probes are of major significance, since an early diagnosis of AD is thereby made possible. With early diagnosis, the disease may already be counteracted at a very early stage.

Such molecular probes comprise the polymer according to the invention and optionally dyes, fluorescent dyes, radioactive isotopes, (PET etc.), gadolinium (MRI), and also alternative substances suitable for imaging the probes and the patients, for example, may be injected intravenously. After passage through the blood-brain barrier, the probes can bind to A-beta oligomers and/or plaques. The A-beta oligomers and/or plaques thus labeled can be visualized by imaging methods such as SPECT, PET, CT, MRT, proton MR spectroscopy etc.

Furthermore, the invention also relates to the use of the peptide for the prevention of amyloid beta oligomers and/or amyloid beta peptide aggregates and/or amyloid beta fibrils.

The peptide according to the invention is also used for the detoxification of toxic amyloid beta oligomers and/or aggregates. Said peptide is particularly used to bind to amyloid beta oligomers and/or aggregates and thus to form amorphous, non-toxic aggregates.

The invention further relates to the use of the peptide according to the invention as a therapeutic agent for Alzheimer's disease.

The peptides according to the invention bind particularly effectively to A-beta oligomers, particularly to soluble A-beta oligomers.

A particularly strong binding of the inventive peptides to the target molecules is caused by high specificity and/or affinity of the inventive peptides for the target molecule. The complexes formed have a low dissociation constant (KD).

By means of the thioflavin T test, it could be shown that the peptides according to the invention very efficiently inhibit the formation of fibrils of A-beta peptides, particularly SEQ ID NO: 1-5, in particular SEQ ID NO: 1 and/or SEQ ID NO: 5.

The invention further relates to the use of the peptides according to the invention in a method for treating (in vitro, ex vivo) blood, blood products and/or organs, characterized in that the blood, the blood products and/or organs are taken from a human or animal body and A(amyloid)-beta oligomers are removed and/or detoxified.

BRIEF DESCRIPTION OF THE DRAWINGS

In the accompanying drawings.

DETAILED DESCRIPTION OF THE PRESENT INVENTION

Examples

1.

The D3 variants listed in Table 1 were chemically synthesized.

TABLE 1

Listing of the D3 derivatives investigated

| Description of the peptide (with explanation) | Amino acid sequence (D-enantiomer) |
|---|---|
| D3 (SEQ ID NO: 11) | rprtrlhthrnr |
| NT-D3 (D3-N-Terminus) (SEQ ID NO: 6) | rprtrl |
| RD1 (rational D3) (SEQ ID NO: 3) | pnhhrrrrrttl |
| RD2 (rational D3) (SEQ ID NO: 2) | ptlhthnrrrrr |
| RD3 (rational D3) (SEQ ID NO: 4) | rrptlrhthnrr |
| D3Δhth (D3 with deletion hth) (SEQ ID NO: 1) | rprtrlrnr |

The effects of the peptides described in the table on A-beta aggregation were investigated by means of density gradient centrifugation. Thus, A-beta was mixed with the respective peptide and the particles formed are separated according to size. The sample to be investigated was placed on the surface of the centrifuge tube in which a density gradient was charged, which consisted of layers of different iodixanol concentrations in this example. During the several hours of separation, the molecules sediment at different rates in the solvent, namely, more rapidly the larger the particles. The centrifugation is terminated at a suitable time point and different constituents of the sample are obtained in the various layers which are analyzed by SDS-PAGE. A-beta without addition of peptide served as control. For example, the evaluation of runs with A-beta and A-beta with RD2 is shown in FIG. 1.

Figure 1:
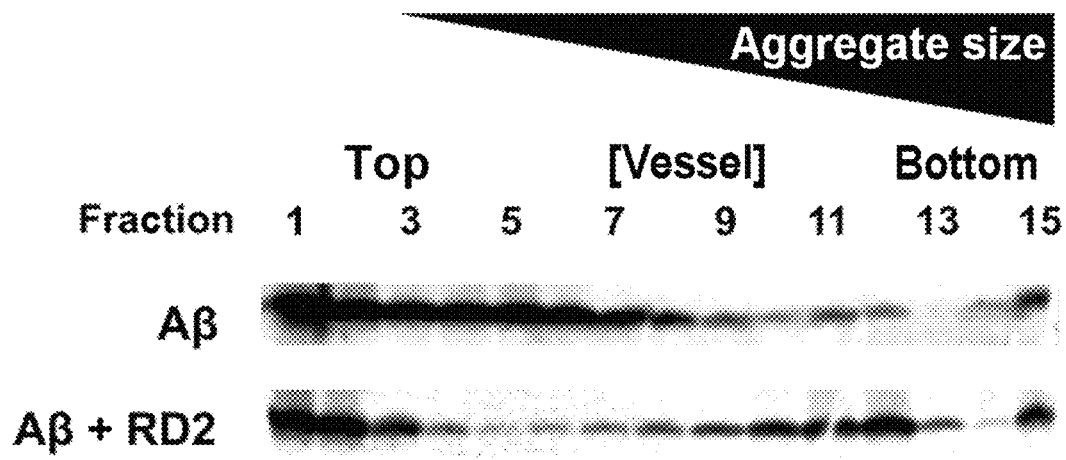
FIG. 1 graphically represents the modulation of the A-beta1-42 aggregation behavior by RD2, analyzed by an iodoxanol gradient as set forth in Example 1 below.

As can be seen in FIG. 1, A-beta could be detected in all fractions in the A-beta sample. This changes on addition of RD2. Here, fewer A-beta oligomers could be detected in the fractions 3-9 (A-beta oligomer fraction). Large aggregates are formed which are detectable in fractions 10-15. D3 showed no effect when the concentration of peptide used was 20 µM. In earlier studies, it was found that D3 in higher concentrations precipitates A-beta oligomers and converts them into large, amorphous and non-toxic aggregates (Funke at al., ACS Chem. Neurosci. 2010). All D-enantiomeric peptides which were characterized with A-beta using the method mentioned above were labelled with FITC. The amount of dye detectable in fraction 12 was used to estimate the binding strength of the respective D3 derivative to A-beta oligomers or the oligomer precipitating effects thereof in vitro. The results for all peptides are shown in Table 2. It was shown that the peptide RD2 especially has a significant effect on A-beta aggregation compared to D3.

TABLE 2

Summary of results of the modulation of the A-beta1-42 aggregation behavior of various D3 derivatives

| Peptide | Peptide bound in fraction 12 [%] |
|---|---|
| A-beta control without peptide | 0 |
| D3 | 4 |
| NT-D3 | 0 |
| RD1 | 3 |
| RD2 | 20 |
| RD3 | 4 |
| D3Δhth | 2 |

2.

Figure 2:
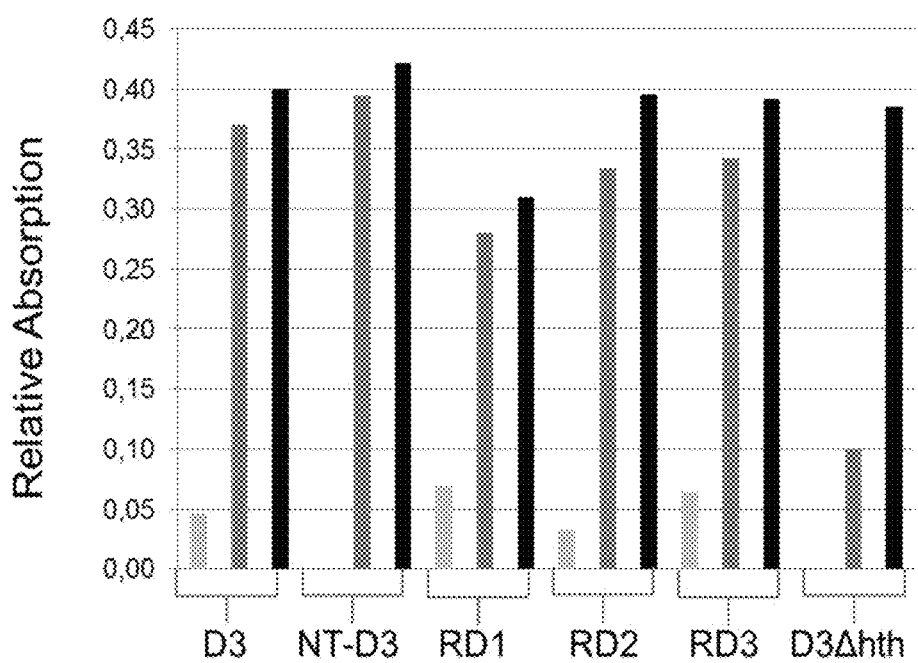
FIG. 2 graphically represents the results of an ELISA assay for the relative quantification of the binding of peptides to various A-beta1-42 conformers as set forth in Example 2 below.

The peptides were also tested with respect to their in vitro binding to various A-beta conformers (A-beta monomers, oligomers, fibrils) using ELISA. All peptides showed weak binding to A-beta monomers but relatively high affinity to oligomers and fibrils (FIG. 2). Interestingly, biotinylated monomers were not detected at the amino terminus, whereas the "seedless" monomers (aggregation seed-free preparation) were weakly bound to the carboxy terminus biotinylation. This may be interpreted as a potential indication of an epitope binding site of the D3 derivatives localized to the amino terminus.

3.

Some peptides were used in the thioflavin T (ThT) aggregation test. ThT is a fluorescent dye which binds to β-sheet-rich structures of various amyloid proteins and fluoresces at 440 nm on excitation. The emission may be correlated in this manner with the relative fibril content in the sample. ThT tests are used for measuring the fibrillation of A-beta and are used especially in ligands to detect potential inhibitory effects of these on A-beta aggregation. The peptides were used in a ratio of 1:10 (A-beta: peptide) with a 10 µM A-beta solution. Fifteen hours later, after reaching the saturation phase in the A-beta control with no addition of ligand, the ThT fluorescence of the co-incubation of D-peptides and A-beta was evaluated and presented as a percentage of the A-beta control incubation. This shows that all peptides used significantly reduce formation of A-beta fibrils (FIG. 3). 4.

Furthermore, D3 variants were identified which have an increased binding strength for A-beta, particularly for A-beta oligomers, with at least the same effect on the aggregation thereof, compared to D3. Stronger binding may suggest a more efficient therapeutic effect.

By means of a PepSpot analysis, using a membrane from JPT (Berlin) on which more than 300 D3 variants had been immobilized, variants were investigated in order to identify which bind with more affinity to A-beta (1-42). D3, D3 variants with varying amino acid sequences (so-called saturation mutagenesis—each amino acid was exchanged with their D-enantiomeric form from all 19 other naturally occurring amino acids) and controls were immobilized on a trioxa membrane carboxy terminal. After the incubation with 5 µM A-Beta(1-42) oligomers for 5 min and washing steps, the signals from bound A-Beta were detected via an anti-A-Beta antibody (6E10). The binding signals were evaluated as signal intensity/area. For the analysis, the signal intensity of the original D3 (mean value) was compared with that of the derivatives. The amino acid exchanges which resulted in stronger binding of A-beta oligomers are summarized in Table 3.

TABLE 3

The D-amino acid sequence of D3 is shown in the first row in bold. In the rows below are listed the type and location of the amino acid exchanges which resulted in an increase in binding strength to A-beta oligomers.

| R | P | R | L | R | L | H | T | H | R | N | R |
|---|---|---|---|---|---|---|---|---|---|---|---|
|   |   | I |   |   | T | P | D |   | Q | Q |   |
|   |   |   |   |   |   | Q |   |   | E | D |   |
|   |   |   |   |   |   | R |   |   |   |   |   |
|   |   |   |   |   |   | S |   |   |   |   |   |

5.

Figure 4:
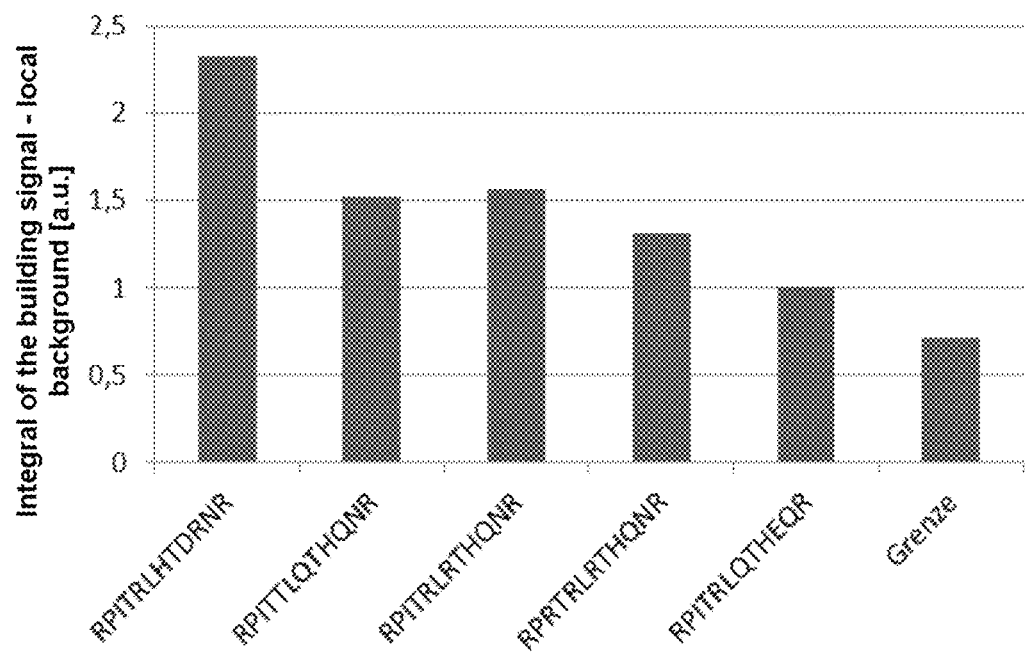
FIG. 4 graphically represents the results of a PepChip experiment as set forth in Example 5 below.

In order to confirm the results and to obtain novel variants with even stronger affinity for A-beta by combination with the amino acid exchanges described in table 4, further D3 variants were coupled to PepChip arrays from Pepscan and their A-beta binding strength was investigated. The selection of the variants were based on the results of the Pepspot membrane evaluation already described. In six independent experiments, the A-beta binding to the D3 derivatives was detected via coupled FITC labeling. In this case, 5 µM A-Beta FITC was used. The detection was performed in a FLA8000 microarray scanner from Fujifilm and the binding signals were measured with the AIDA Array Metrix Software and evaluated with the aid of Mathlab Version 7.10.0.449. FIG. 4 shows the binding signals of a selected PepChip as example.

Five of the peptides immobilized on the PepChips exceeded the limit in at least four of six experiments and thus showed considerably higher binding affinity to A-beta compared to D3. These peptide sequences are summarized in Tab. 4. Among these, sequences with combined exchanges can be found from Tab. 3.

TABLE 4

Sequences of the D-peptides having stronger A-beta monomer binding strength compared to D3

| Sequence | Name |
|---|---|
| RPITRLHTDRNR (SEQ ID NO: 7) | DB1 |
| RPITTLQTHQNR (SEQ ID NO: 8) | DB2 |
| RPITRLRTHQNR (SEQ ID NO: 5) | DB3 |
| RPRTRLRTHQNR (SEQ ID NO: 9) | DB4 |
| RPITRLQTHEQR (SEQ ID NO: 10) | DB5 |

DESCRIPTION OF THE FIGURES

FIG. 1: Modulation of the A-beta1-42 aggregation behavior by RD2, analzyed by an iodixanol density gradient. The iodixanol gradient was overlayed with 100 µl of a 80 µM A-beta1-42 solution and 100 µl of a 80 µM A-beta and 20 µM RD2 mixture. The mixture was then centrifuged at 259,000×g for 3 h at 4° C. The 15 fractions (fraction 15 is the pellet boiled with the loading buffer) were harvested manually immediately after the centrifugation and analyzed by Tris-Tricin-SDS-PAGE followed by silver staining. If the run was carried out under identical conditions with 20 µM D3, no change was apparent compared to the run with only A-beta.

FIG. 2: ELISA for the relative quantification of the binding of the peptides to various A-beta1-42 conformers. Seedless monomers of carboxy terminal biotinylated A-beta (light grey bars) and oligomers (dark grey bars) and fibrils (black bars) of amino terminal biotinylated A-beta monomers were each immobilized at 5 µg/ml and the D-peptide applied at a concentration of 10 µg/ml. The relative quantification of the binding of the peptides in a duplicate determination is shown as absorption at 450 nm after subtraction of the background absorption.

Figure 3:
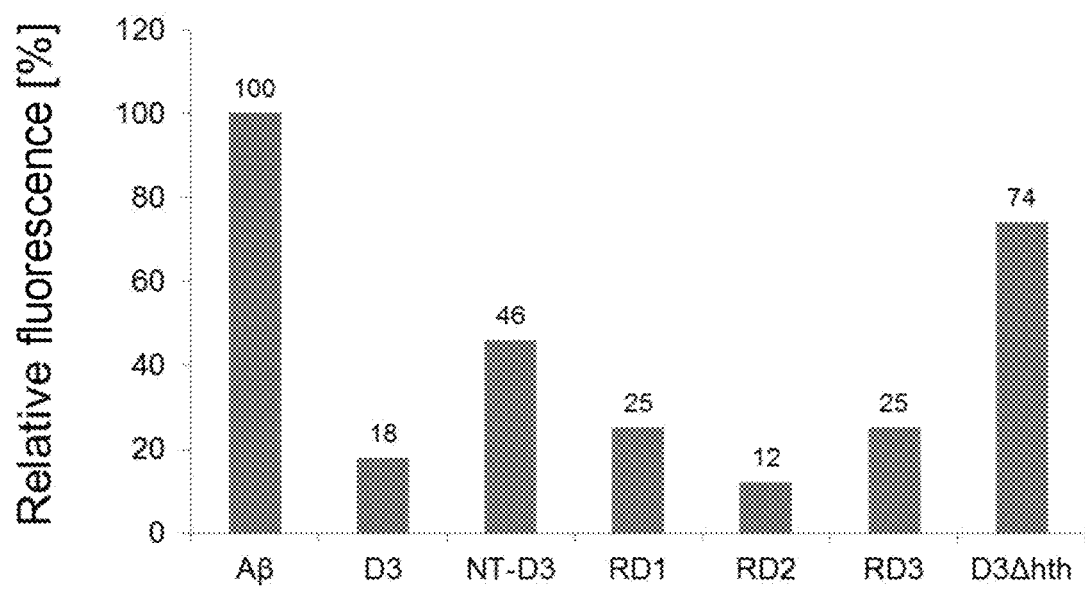
FIG. 3 graphically represents the results of a ThT aggregation test for A-beta1-42 for the quantification of the relative fibril content in the presence of various peptides as set forth in Example 3 below.

FIG. 3: ThT aggregation test of A-beta1-42 for the quantification of the relative fibril content in the presence of various peptides. The concentration of A-beta was 10 µM and the peptides were added in a ratio of 1:10 (A-beta: peptide). The fluorescence of 10 µM A-beta was set to 100% and the values and standard deviations of the other incubations are given as percentages of this maximum value. None of the petides showed a significant ThT fluorescence with no A-beta.

FIG. 4: Results of a PepChip experiment. Different D3 variants were immobilized on the PepChip. The PepChip was incubated with FITC labeled A-beta (5 µM). The FITC fluorescence intensity was read as a measure of the binding strength of the respective D3 derivatives. Values of the mean and standard deviation were calculated from the 11 values obtained for the D3 controls likewise applied at 11 different positions on the chip. Mean and standard deviation were added and the result was defined as the limit which a D3 derivative must attain in order to clearly have higher affinity for A-beta compared to D3. The integrals of the binding signals of all peptides are shown which exceed this limit. The individual bars are based on the means of three exactly identical peptide spots. a.u.: arbitrary units, relative fluorescence units. Due to the observed variance in the results, this entire experiment was carried out six times.

What is claimed is:

1. A peptide containing at least one amino acid sequence, wherein the peptide comprises at least 50% D-enantiomeric amino acids and the at least one amino acid sequence is SEQ ID NO: 5 or a homolog thereof with a sequence identity of at least 83%.

2. The peptide of claim 1, wherein the peptide is substantially composed of D-amino acids.

3. The peptide of claim 1, wherein the peptide is capable of inhibiting formation of fibrils of amyloid beta peptides.

4. The peptide of claim 1, wherein the peptide is capable of binding to aggregated amyloid beta peptides.

5. The peptide of claim 1, wherein the peptide is capable of being used as a therapeutic agent in medicine.

6. The peptide of claim 1, wherein the peptide is capable of treating Alzheimer's disease.

7. A pharmaceutical composition, wherein the composition comprises as one of the components thereof the peptide of claim 1.

8. A probe for the identification and quantitative and/or qualitative determination of amyloid beta fibrils and/or amyloid beta oligomers, wherein the probe comprises the peptide of claim 1.

9. A kit, wherein the kit comprises the peptide of claim 1.

10. The peptide of claim 1, wherein the peptide is linked to a further substance.

11. The peptide of claim 1, wherein the at least one amino acid sequence is SEQ ID NO: 5.

12. A pharmaceutical composition, wherein the composition comprises as one of the components thereof the peptide of claim 11.

13. A probe for the identification and quantitative and/or qualitative determination of amyloid beta fibrils and/or amyloid beta oligomers, wherein the probe comprises the peptide of claim 11.

14. A kit, wherein the kit comprises the peptide of claim 11.

15. A method for the detoxification of toxic amyloid beta oligomers and/or aggregates, wherein the method comprises contacting the oligomers and/or aggregates with the peptide of claim 11.

16. A method for preparing the peptide of claim 1, wherein the method involves peptide synthesis or mutagenesis.

17. A method for the detoxification of toxic amyloid beta oligomers and/or aggregates, wherein the method comprises contacting the oligomers and/or aggregates with the peptide of claim 1.

18. The method of claim 17, wherein the amyloid beta oligomers and/or aggregates form amorphous, non-toxic aggregates with the peptide.

* * * * *

SEQUENCE LISTING

<160> NUMBER OF SEQ ID NOS: 11

<210> SEQ ID NO 1
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(9)
<223> OTHER INFORMATION: D-amino acid

<400> SEQUENCE: 1

Arg Pro Arg Thr Arg Leu Arg Asn Arg
1               5

<210> SEQ ID NO 2
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(12)
<223> OTHER INFORMATION: D-amino acid

<400> SEQUENCE: 2

Pro Thr Leu His Thr His Asn Arg Arg Arg Arg Arg
1               5                   10

<210> SEQ ID NO 3
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(12)
<223> OTHER INFORMATION: D-amino acid

<400> SEQUENCE: 3

Pro Asn His His Arg Arg Arg Arg Arg Thr Thr Leu
1               5                   10

<210> SEQ ID NO 4
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(12)
<223> OTHER INFORMATION: D-amino acid

<400> SEQUENCE: 4

Arg Arg Pro Thr Leu Arg His Thr His Asn Arg Arg
1               5                   10

<210> SEQ ID NO 5
<211> LENGTH: 12
<212> TYPE: PRT
<213> ORGANISM: Artificial Sequence

```
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(12)
<223> OTHER INFORMATION: D-amino acid

<400> SEQUENCE: 5

Arg Pro Ile Thr Arg Leu Arg Thr His Gln Asn Arg
1               5                   10

<210> SEQ ID NO 6
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(6)
<223> OTHER INFORMATION: D-amino acid

<400> SEQUENCE: 6

Arg Pro Arg Thr Arg Leu
1               5

<210> SEQ ID NO 7
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(12)
<223> OTHER INFORMATION: D-amino acid

<400> SEQUENCE: 7

Arg Pro Ile Thr Arg Leu His Thr Asp Arg Asn Arg
1               5                   10

<210> SEQ ID NO 8
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(12)
<223> OTHER INFORMATION: D-amino acid

<400> SEQUENCE: 8

Arg Pro Ile Thr Thr Leu Gln Thr His Gln Asn Arg
1               5                   10

<210> SEQ ID NO 9
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(12)
<223> OTHER INFORMATION: D-amino acid
```

```
<400> SEQUENCE: 9

Arg Pro Arg Thr Arg Leu Arg Thr His Gln Asn Arg
1               5                   10

<210> SEQ ID NO 10
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(12)
<223> OTHER INFORMATION: D-amino acid

<400> SEQUENCE: 10

Arg Pro Ile Thr Arg Leu Gln Thr His Glu Gln Arg
1               5                   10

<210> SEQ ID NO 11
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(12)
<223> OTHER INFORMATION: D-amino acid

<400> SEQUENCE: 11

Arg Pro Arg Thr Arg Leu His Thr His Arg Asn Arg
1               5                   10
```